(12) United States Patent
Stecco et al.

(10) Patent No.: US 11,033,308 B2
(45) Date of Patent: Jun. 15, 2021

(54) ACTIVE BONE AND JOINT STABILIZATION DEVICE FEATURES

(71) Applicant: PANTHER ORTHOPEDICS, INC., Sunnyvale, CA (US)

(72) Inventors: Kathryn A. Stecco, San Jose, CA (US); Frank P. Becking, Los Gatos, CA (US); Carlos Castro, San Jose, CA (US)

(73) Assignee: PANTHER ORTHOPEDICS, INC., Sunnyvale, CA (US)

( * ) Notice: Subject to any disclaimer, the term of this patent is extended or adjusted under 35 U.S.C. 154(b) by 182 days.

(21) Appl. No.: 16/032,736

(22) Filed: Jul. 11, 2018

(65) Prior Publication Data

US 2019/0046253 A1 Feb. 14, 2019

Related U.S. Application Data

(60) Provisional application No. 62/543,272, filed on Aug. 9, 2017.

(51) Int. Cl.
*A61B 17/84* (2006.01)
*A61B 17/68* (2006.01)
(Continued)

(52) U.S. Cl.
CPC ........ *A61B 17/842* (2013.01); *A61B 17/0401* (2013.01); *A61B 17/06166* (2013.01); *A61B 17/683* (2013.01); *A61B 17/8635* (2013.01); *A61L 31/06* (2013.01); *A61B 2017/00115* (2013.01); *A61B 2017/00119* (2013.01);
(Continued)

(58) Field of Classification Search
CPC ....... A61B 17/84; A61B 17/842; A61B 17/86; A61B 17/8635; A61B 17/04; A61B 17/0401; A61L 31/06
See application file for complete search history.

(56) References Cited

U.S. PATENT DOCUMENTS 3,717,906 A 2/1973 Wells
3,880,166 A 4/1975 Fogarty
(Continued)

FOREIGN PATENT DOCUMENTS

CN 1631325 A 6/2005
DE 19527151 1/1997
(Continued)

OTHER PUBLICATIONS

WO, PCT/US2018/041620 ISR and Written Opinion, dated Nov. 22, 2018.
(Continued)

*Primary Examiner* — Christopher J Beccia
(74) *Attorney, Agent, or Firm* — Kurt T. Mulville; VLP Law Group, LLP

(57) ABSTRACT

Components and associated methods of manufacture or assembly and/or use for bone and joint stabilization devices or systems are described. The components include features for device introduction, attaching a distal anchoring foot or threaded screw to an elongate spring-type member, anchoring head features for stabilizing position of the elongate member when engaged within the head and/or digital or electronic methods for tensioning the subject devices.

23 Claims, 5 Drawing Sheets

(51) Int. Cl.
*A61B 17/06* (2006.01)
*A61B 17/04* (2006.01)
*A61B 17/86* (2006.01)
*A61L 31/06* (2006.01)
*A61B 90/00* (2016.01)
*A61B 17/00* (2006.01)

(52) U.S. Cl.
CPC ............ *A61B 2017/00128* (2013.01); *A61B 2017/00367* (2013.01); *A61B 2017/044* (2013.01); *A61B 2017/0404* (2013.01); *A61B 2017/0414* (2013.01); *A61B 2017/0417* (2013.01); *A61B 2017/0448* (2013.01); *A61B 2017/0462* (2013.01); *A61B 2017/0618* (2013.01); *A61B 2017/681* (2013.01); *A61B 2090/064* (2016.02); *A61B 2090/3966* (2016.02)

(56) References Cited

U.S. PATENT DOCUMENTS

| | | | |
|---|---|---|---|
| 4,377,872 A | 3/1983 | Daniell, Jr. | |
| 4,680,834 A * | 7/1987 | Andre | F16L 3/2336 24/16 PB |
| 4,688,561 A | 8/1987 | Reese | |
| 4,959,064 A | 9/1990 | Engelhardt | |
| 5,258,015 A | 11/1993 | Li et al. | |
| 5,370,646 A | 12/1994 | Reese et al. | |
| 5,415,660 A | 5/1995 | Campbell et al. | |
| 5,500,018 A | 3/1996 | Spotorno et al. | |
| 5,549,619 A | 8/1996 | Peters et al. | |
| 5,810,854 A | 9/1998 | Beach | |
| 6,080,154 A | 6/2000 | Reay-Young et al. | |
| 6,093,190 A | 7/2000 | Mattchen | |
| 6,193,754 B1 | 2/2001 | Seedhom | |
| 6,293,949 B1 | 9/2001 | Justis et al. | |
| 6,656,184 B1 | 12/2003 | White et al. | |
| 7,008,429 B2 | 3/2006 | Golobek | |
| 7,235,091 B2 | 6/2007 | Thornes | |
| 7,285,086 B2 | 10/2007 | Smith et al. | |
| 7,833,256 B2 | 11/2010 | Biedermann et al. | |
| 7,875,057 B2 | 1/2011 | Cook et al. | |
| 7,985,222 B2 | 7/2011 | Gall et al. | |
| 8,048,134 B2 | 11/2011 | Partin | |
| 8,348,960 B2 | 1/2013 | Michel et al. | |
| 8,449,574 B2 | 5/2013 | Biedermann et al. | |
| 8,491,583 B2 | 7/2013 | Gall et al. | |
| 8,535,358 B2 | 9/2013 | Willert et al. | |
| 8,597,300 B2 | 12/2013 | Deffenbaugh et al. | |
| 8,771,316 B2 | 7/2014 | Denham et al. | |
| 8,828,067 B2 | 9/2014 | Tipirneni et al. | |
| 10,194,946 B2 | 2/2019 | Stecco et al. | |
| 2002/0019634 A1 | 2/2002 | Bonutti | |
| 2002/0091391 A1 | 7/2002 | Cole et al. | |
| 2005/0085815 A1 | 4/2005 | Harms et al. | |
| 2005/0203519 A1 | 9/2005 | Harms et al. | |
| 2006/0195103 A1 | 8/2006 | Padget et al. | |
| 2006/0264944 A1 | 11/2006 | Cole | |
| 2006/0264954 A1 | 11/2006 | Sweeney, II et al. | |
| 2008/0172097 A1 | 7/2008 | Lerch et al. | |
| 2008/0275555 A1 | 11/2008 | Makower et al. | |
| 2008/0281339 A1 * | 11/2008 | Kirschman | A61B 17/688 606/151 |
| 2008/0287991 A1 | 11/2008 | Fromm | |
| 2010/0082072 A1 | 4/2010 | Sybert et al. | |
| 2010/0094347 A1 | 4/2010 | Nelson et al. | |
| 2010/0211071 A1 | 8/2010 | Lettmann et al. | |
| 2010/0292793 A1 | 11/2010 | Höglund | |
| 2011/0125194 A1 | 5/2011 | Anwand et al. | |
| 2012/0203284 A1 | 8/2012 | Khanna | |
| 2012/0232597 A1 | 9/2012 | Saidha et al. | |
| 2013/0079776 A1 | 3/2013 | Zwirkoski et al. | |
| 2013/0079778 A1 | 3/2013 | Azuero et al. | |
| 2013/0261625 A1 | 10/2013 | Koch et al. | |
| 2014/0100573 A1 | 4/2014 | Llas Vargas et al. | |
| 2014/0228883 A1 | 8/2014 | Blain | |
| 2014/0257294 A1 * | 9/2014 | Gedet | A61B 17/0401 606/80 |
| 2015/0045794 A1 | 2/2015 | Garcia et al. | |
| 2015/0238232 A1 | 8/2015 | Biedermann et al. | |
| 2016/0100947 A1 | 4/2016 | Carvani et al. | |
| 2016/0213368 A1 | 7/2016 | Stecco et al. | |
| 2017/0281150 A1 | 10/2017 | Stecco et al. | |
| 2019/0117265 A1 | 4/2019 | Stecco et al. | |

FOREIGN PATENT DOCUMENTS

| | | |
|---|---|---|
| JP | 2003-220071 A1 | 8/2003 |
| WO | WO 2008/016910 A2 | 2/2008 |
| WO | WO 2014/149244 A1 | 9/2014 |
| WO | WO 2016/122944 A1 | 8/2016 |
| WO | WO 2019/032231 A1 | 2/2019 |

OTHER PUBLICATIONS

EP, 16743868.8 Extended Searh Report, dated Dec. 8, 2017.
CN, 201680007323.0 Office Action, dated Oct. 21, 2019.
JP, 2017-557276 Office Action, dated Oct. 21, 2019.
WO, PCT/US2016/014125 ISR and Written Opinion, dated May 13, 2016.
WO, PCT/US2017/024768 ISR and Written Opinion, dated Jul. 20, 2014.

* cited by examiner

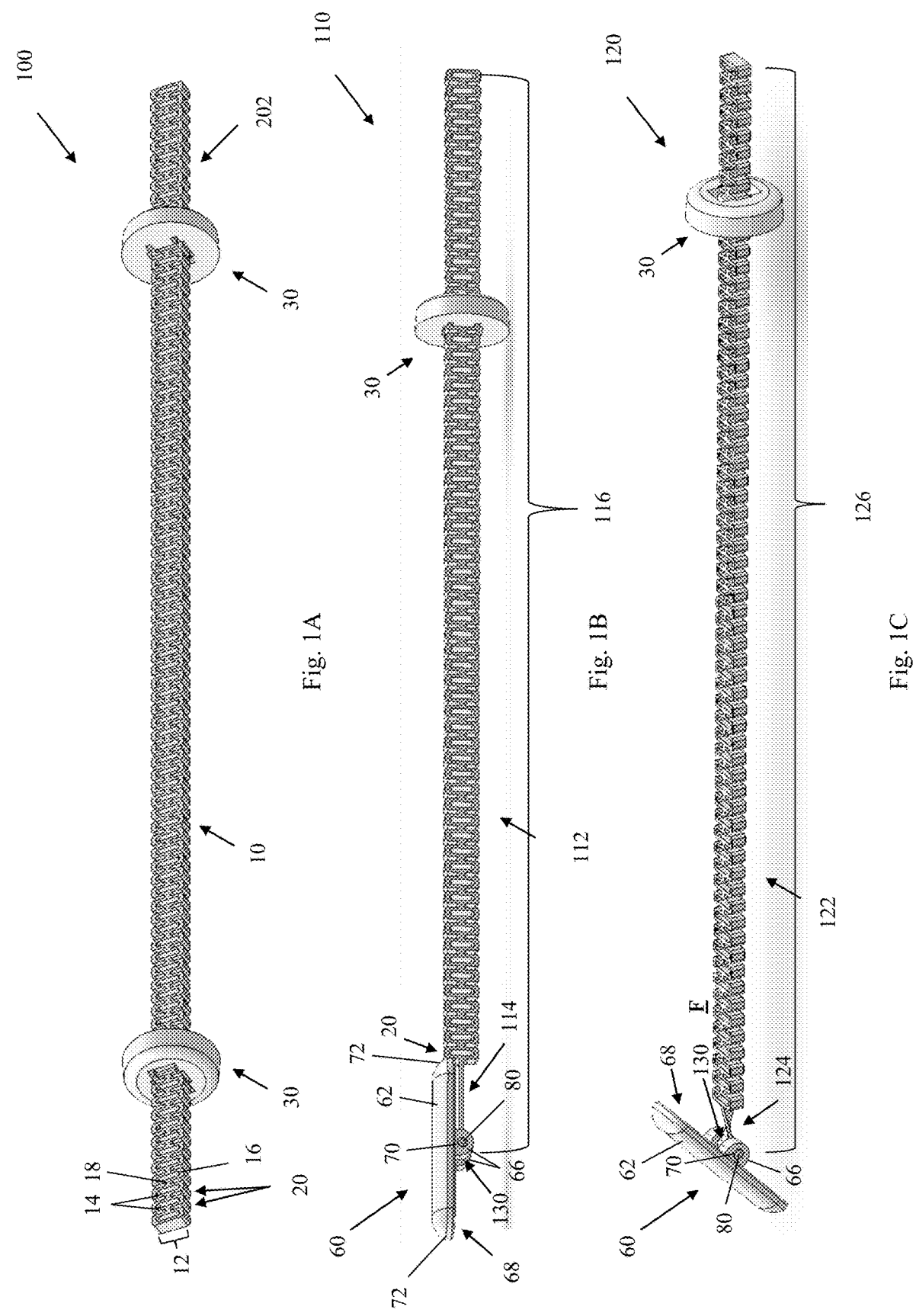

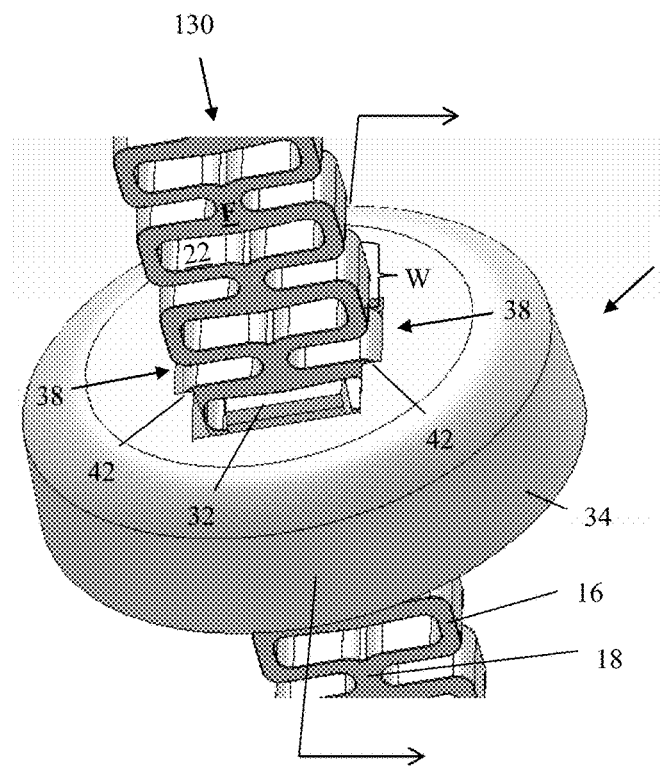 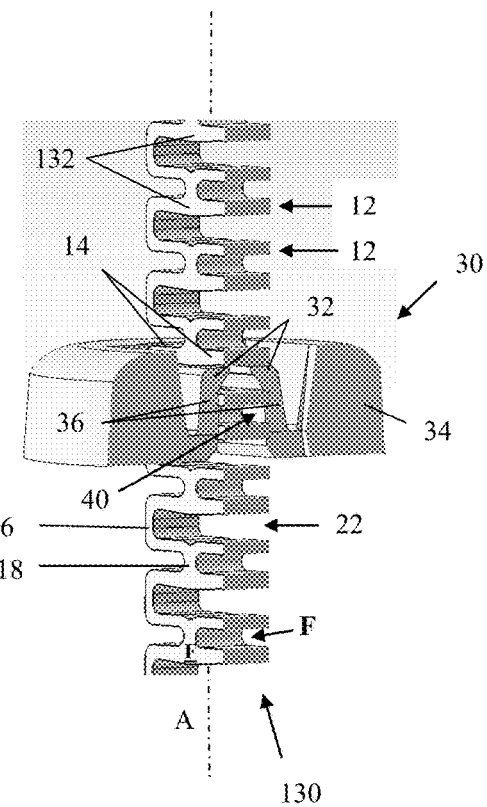
Fig. 2A  Fig. 2B
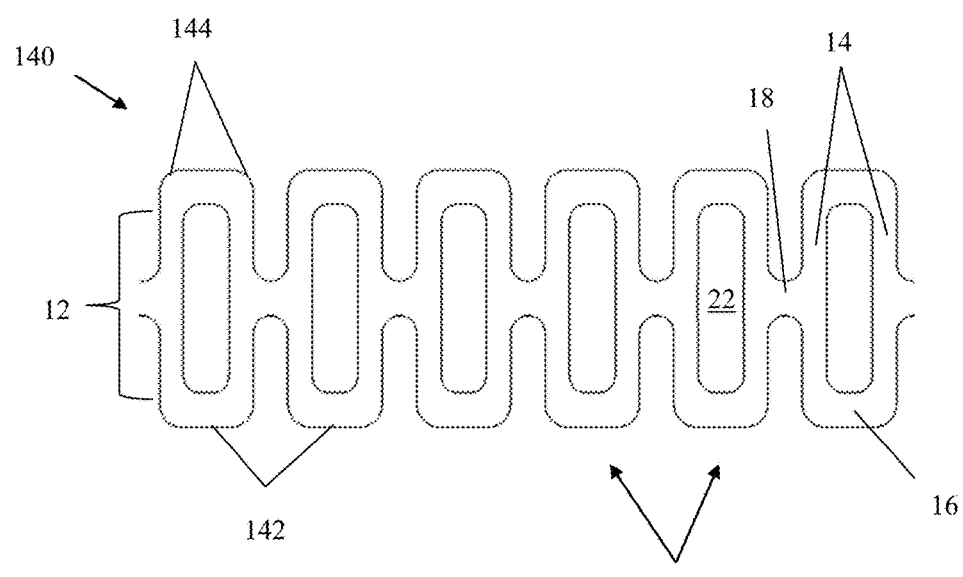
Fig. 3

US 11,033,308 B2

ACTIVE BONE AND JOINT STABILIZATION DEVICE FEATURES

RELATED APPLICATIONS

This application claims the benefit of and priority to U.S. Provisional Patent Application Ser. No. 62/543,272, filed Aug. 9, 2017, and entitled, "BONE AND JOINT STABILIZATION ATTACHMENT FEATURES," which is incorporated herein by reference in its entirety for any and all purposes.

FIELD

The embodiments described herein are related in the field of surgery and, more particularly, for use in bone fusion, joint stabilization and/or fracture fixation surgery.

BACKGROUND

Various devices have been employed in orthopedic surgery for bone fusion and/or joint stabilization. Bone screws, staples and plates have served as a set of rigid options. U.S. Pat. Nos. 4,959,064; 6,656,184; 7,833,256; 7,985,222; 8,048,134; 8,449,574 and 8,491,583, as well as U.S. Publication No. 2006/0264954, describe examples of screw-type devices with incorporated tensioning springs or members. Button-and-suture type devices have provided a more flexible set of options, examples of which are described in U.S. Pat. Nos. 7,235,091; 7,875,057 and 8,348,960. However, the aforementioned examples have many shortcomings, and needs exist to address these shortcomings and others.

SUMMARY

Provided herein are example embodiments of bone and/or joint stabilization devices that can be tensioned during a medical procedure to remain active in maintaining compression of the subject anatomy during use. In many embodiments, an orthopedic surgery device or system includes an elongate member or body, optionally including a spring pattern having a plurality of beams, each including a lateral component free to deflect when stretching the elongate body axially. An anchoring head can receive the elongate body and may secure it with a one-way (e.g., ratcheting) interface. Two such anchors may be used, or one such anchor may be used with a deployable foot or screw anchor used to anchor an opposite end of the elongate body. Details of elongate spring members, as well as anchoring head and foot features, are further set forth in US Publication No. 2016/0213368 ("Active Tension Bone and Joint Stabilization Devices") and Int'l Publication No. WO 2016/122944 ("Active Tension Bone and Joint Stabilization Devices") both of which are incorporated by reference herein in their entities for all purposes. Suitable methods of medical use also applicable to the present embodiments are described with respect to FIGS. 8-15 of the incorporated U.S. Publication No. 2016/0213368 and Int'l Publication No. WO 2016/122944.

Many embodiments described herein include optional elongate spring member features as well as optional aspects associated with the anchoring head, anchoring foot and a screw-type anchor (e.g., the attachment features). Digital or electronic tensioning method and system embodiments are also described.

Various assembled parts may be provided in packaged combination in a kit to be acquired by the medical professional. The elongate spring member may be loaded in a sheath with a portion of an anchoring foot to position the anchoring foot in alignment with the elongate body for implantation. In producing a final assembly (e.g., carried out by a physician in situ), the elongate spring member or body may be received at a proximal end by an anchoring head. A tooth or multiple teeth in an anchoring head may be engaged with the elongate spring member and advanced relative to the spring member or body until it is stretched to a desired tension. Tooth engagement may be with through-holes in the elongate spring member or body. Finally, the elongate spring member may be trimmed to length with flush cutters or a customized unit in either a method of use and/or manufacture of a final implant configuration.

In sum, the subject device or systems, kits in which they are included (with or without assembly), methods of use (e.g., with implantation, during treatment of a patient while mending and/or for system removal) and manufacture (including assembly of the various components—as applicable—by a technician prior to sale or during a medical procedure by a surgeon) are all included within the scope of the present disclosure.

BRIEF DESCRIPTION OF THE DRAWINGS

The details of the subject matter set forth herein, both as to its structure and operation, may be apparent by study of the accompanying figures, in which like reference numerals may refer to like parts. The components in the figures are not necessarily to scale, emphasis instead being placed upon illustrating the principles of the subject matter. The illustrations are intended to convey concepts, where relative sizes, shapes and other detailed attributes may either be illustrated schematically rather or precisely. To-scale features (e.g., as from engineering drawings and/or photographs) may be relied upon as antecedent basis for claim support.

FIGS. 1A-1C are side-perspective views of different example embodiments of the subject medical devices or systems.

FIGS. 2A and 2B are perspective detail and cross-sectional views, respectively, of example embodiments of the elongate spring member and an anchoring head configuration.

FIG. 3 is a face or top view of a section of an example embodiment of an elongate spring member pattern.

DETAILED DESCRIPTION

Figures 4A, 4B:
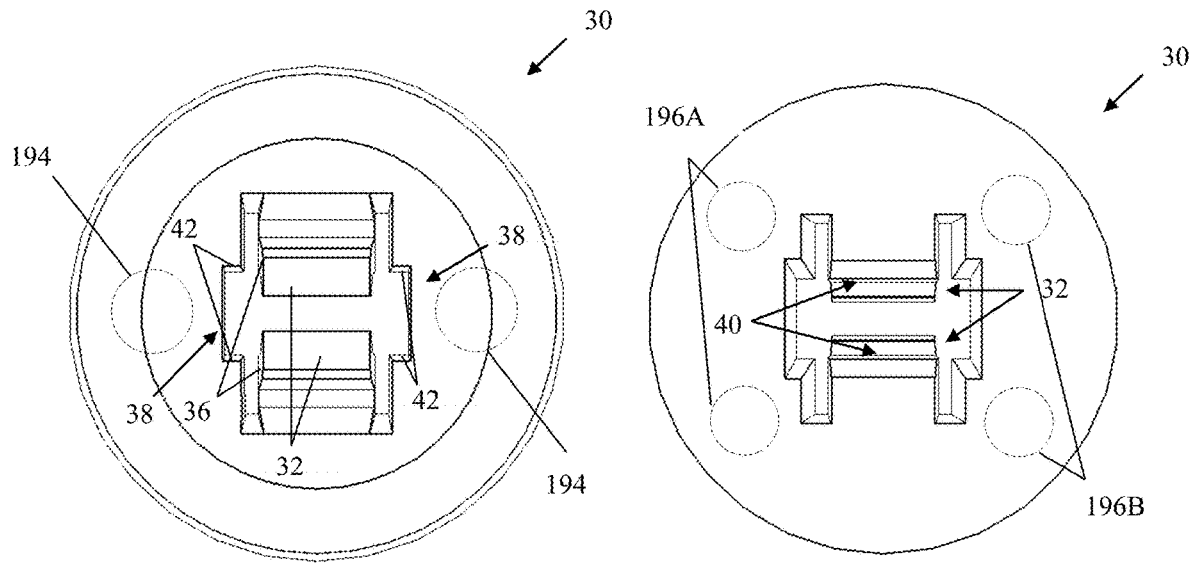
FIGS. 4A-4C are top, bottom and a side section (with detail) views, respectively, of an example embodiment of the anchoring head shown in FIGS. 2A and 2B.

Various example embodiments are shown in the figures and further described below. Reference is made to these examples in a non-limiting sense, as it should be noted that they are provided to illustrate more broadly applicable aspects of the devices, systems and/or methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present invention. All such modifications are intended to be within the scope of the claims that can be made herein.

The subject methods, including methods of use and/or manufacture, may be carried out in any order of the events which is logically possible, as well as any recited order of events. Medical methods may include any of a hospital staffs activities associated with device provision, implant introduction, positioning and/or re-positioning, and surgical access, closure and/or removal (e.g., as in an explant procedure).

EXAMPLE EMBODIMENTS

Example embodiment 100 in FIG. 1A includes an elongate spring member or body 10 in the form of a stretchable or spring-type architecture including multiple beams or beam members 12. The beams 12 can each include a lateral component free to deflect for stretching the spring member axially. In the spring pattern, lateral bars 14 are provided in opposing pairs joined to each other at an outer extent connector 16 of each beam. Each such connector 16 may be a curved continuation of each bar 14 or beam 12 or otherwise configured (e.g., as described in connection with FIG. 3). Each pair of beams 12 is connected to an axially adjacent pair by a medial connector or bridge 18. The beams 12 or beam pairs serve as leaf spring elements in series that are arranged in cells 20.

Embodiments 110 and 120 in FIGS. 1B and 1C include similar spring member sections 112 and 122, respectively. These embodiments also each include a longitudinal extension section 114 and 124, respectively. Together the spring and the axial or longitudinal extension sections define an overall elongate body 116 and 126 for each of embodiments 110 and 120, respectively.

Embodiments 110 and 120 employ different anchoring features than in embodiment 100. In embodiment 100, two opposite-facing one-way anchor heads 30 are used. Heads 30 are "one-way" because they are configured to be readily advanced along cells 20 in only one direction, and are configured to resist movement in the opposite direction, e.g., like a ratchet or zip-tie head. In embodiments 110 and 120, only one anchor or anchoring head 30 is used together with a pivoting foot anchor 60. Embodiment 110 includes a straight extension 114 from its spring member section 112. Embodiment 120 includes a twisted extension 124 from its spring member section 122. A socket 130 with a through hole or aperture (not shown) is formed at the end of each extension.

The anchor or anchoring foot 60 in each of embodiments 110 and 120 may include a body 62 with an oval, race-track or rectangular planform shape. Generally, the height, length and width of foot 60 will be minimized while still maintaining adequate surface area and strength for load bearing. The distal or outboard surface 64 of foot 60 may be fully radiused to decrease crossing profile and/or to improve or enhance the interface with overlying tissue without significant loss of strength.

Projections or bosses 66 extend above a proximal or inboard surface 68 of foot 60. A transverse hole 70 is formed in each boss 66. A pin 80 is received through each of through holes 70 and an aperture in the extensions 114/124 to attach each foot 60 in embodiments 110 and 120. An interference or press fit can be advantageously employed between pin 80 and the aperture in extension 114/124 while the through holes 70 in bosses 66 remain free to pivot or spin around pin 80. Alternatively, bosses 66 may be configured for an interference fit with pin 80 with rotation allowed through the aperture in extension 114/124.

In the case of embodiment 110, its extension 114 can be laser cut (or otherwise manufactured) with pin-hole socket 130 produced along with spring member section 112. In embodiment 120, the extension 124 with socket 130 is formed straight, followed by heatsetting to achieve a stable, final configuration that includes a twist or offset (e.g., 45-90 degrees). In some embodiments, when the elongate member or body 126 is produced in NiTi alloy, the heatsetting may be accomplished by exposing the material to 500-550° C. for up to about 5 minutes in a furnace or salt bath while held twisted in a jig or otherwise.

The configuration with a twist heatset into extension 124 allows foot anchor 60 to "stow" flat against elongate body 122. Or stated otherwise, the proximal surface 68 of anchoring foot 60 aligns with a face (F) of the spring member section 122 when the foot is pivoted for deployment. Without the twist, extension 114 can be advantageously sized in length so that the tip(s) or end(s) 72 of the foot anchor fit adjacent to beam segments 16 of spring member section 112 adjacent to (rather than overlapping) the terminal cell 20 of the spring member section—as shown in the example of FIG. 1B.

Because of the 90 degree "phase" difference of orientation for the foot relative to spring member section 112/122 in each of embodiments 110 and 120, one may be selected instead of another for treating a given type of orthopedic injury. Stated otherwise, a surgeon may select and/or orient or "clock" the device preferentially in one direction or the other in order to offer greater stabilization and/or mobility around a selected axis (given any difference in lateral flexibility between different orientations of the spring member).

Regardless of the embodiment selected, the pinned-on-foot embodiments of FIGS. 1B and 1C are advantageous in terms of their robust connection and ease of precision manufacture. So-connected or affixed, the anchoring foot 60 can rotate from a position aligned with the elongate body 112/122 to a position transverse (or at least angled, typically upwards of about 45 or about 60 degrees up to 90 degrees) to the elongate body 112/122 for anchoring the overall device during a medical procedure. Complicating features (e.g., means providing a bias towards the transverse position by an integral or a supplemental spiral spring to aid transition from the foot's axial delivery configuration to its implanted position) may be provided. Alternatively, one or more pull wires or cords may be employed to accomplish or assist with such rotation.

The elongate body 112/122 in the subject embodiments may be covered by a sheath prior to deployment. If implanted, the sheath may prevent tissue ingrowth. Alternatively, the sheath may be used to support the elongate body 112/122 for advancement into place and/or hold distal anchor (e.g., anchoring foot) position. The sheath may be trimmed to desired length before or after any such activity, or it may be selected from a panel of different length pre-trimmed sheaths. It may be removed as part of an overall orthopedic injury treatment method along with the elongate member and head and foot anchors, after healing. Or the sheath may be left in place, serving the purpose of allowing removal of the elongate member as part of this or these method(s) or as a separate removal procedure method.

In FIGS. 2A and 2B, detailed aspects of the anchoring head 30 in FIGS. 1A-1C are shown. As stated above, the anchor or anchoring head 30 is designed for one-way advancement over the spring member body 10 or body section 112, 126, etc. As shown, at least one tooth 32 in each anchoring head interacts with the apertures or windows 22 defined within each cell 20 of the spring body or portion.

The overall shape of the anchor head body 34 may be round, square or otherwise configured. Indeed, the support structure (e.g., the body) for included support columns 36 and teeth 32 in a given anchor head may be integrated in an orthopedic plate (e.g., as integrally formed or press-fit therein) or otherwise provided. As illustrated with included draft angles, anchor 30 can be advantageously injection molded in biocompatible poly-ether-ether-ketone (PEEK) polymer material. Nevertheless, other anchor and/or coordinated body configurations or constructions may be employed in the subject devices or systems.

With respect to the elongate spring member section 130 shown, the cells 20 in the spring pattern can include a pre-set curve 132 for tooth interface. The curve flattens when under stress to provide a relatively more flattened, stress-reducing interface with the anchor head teeth 32 when at high stress and/or strain. Another optional feature involves cutouts 134 included to increase beam flexibility adjacent to medial bridge or connector 18 between adjacent sets of bars or beam sections 16.

If such features are used in a system 100 with two anchoring heads 30 (that can be configured the same but applied to the elongate spring member 10 facing in opposite directions) their pattern can be reversed, e.g., can have a mirror image pattern on each side of the elongate body.

However, neither of these features are essential. A flat beam architecture of the elongate spring body 10 or elongate spring member section 112/122 may be used like that illustrated and further described in connection with FIG. 3.

Regardless, the cutaway view of the beams in FIG. 2B shows that the beams 12 largely lie within planes that are substantially orthogonal to an axis (A) of the elongate spring member section 130. The same relation holds for the other spring member bodies and sections 10/112/122, etc. shown herein.

Regarding the anchoring head 30 shown in FIGS. 2A and 2B, it employs opposing teeth 32 shown engaged across the lateral bars 14 that make up the beams 12 of the spring body section 130. Guide slots, troughs or channels 38 are provided. These slots 38 may be full-length or full-height (minus any introduction radius, chamfer or taper) relative to the anchoring head body 34 and configured to closely fit the width (W) of the elongate spring member section. This fore-aft or front-to-back face clearance of the sides of elongate body section 130 within the slots 38 is minimized to the extent possible given manufacturing tolerances to provide only a close slip fit. Accordingly, about 0.005 inches overall gap or clearance is provided. Preferably, between 0.002 to 0.003 inches gap or clearance is provided at the tightest point. Lateral or side-to-side clearance of the elongate spring member section 130 in the guide slots 38 may be similarly minimized.

In addition, the support columns 36 for the teeth in the subject anchoring heads 30 are configured with an inner surface 40 that parallels the side faces 42 of the slot 38 as much as possible (e.g., given molding draft angle considerations). Stated otherwise, the columns or beams 36 supporting or carrying the teeth 32 are configured (minus any introduction radius, chamfer or taper) to provide outward (fore-and-aft) support to the faces (F) of elongate spring member section 130 (e.g., for at least about 40% of the height of the anchoring head, up to 60% or more) together with the sides 42 of the guide slot 38. As such, the support columns 36 can work in conjunction with the channels or slot 38 to provide robust constrain in positioning the elongate spring member section 130 (or other examples 10, 112, 122, etc.) therebetween.

The guide slots 38 and support column surfaces 40 (alone and/or in combination) can be important in maintaining both teeth 32 engaged with a spring member beam 12 when the anchor head 30 is canted or set at an angle as it rests on a plate or anatomy adjacent the ends of a guide hole drilled in bone. Without the support column constraint, flex in the elongate member 10 or spring member section 112/122/130 (or 140/152/162, 182 as referenced below) could cause disengagement from fine or small slot features 38 when the elongate spring member or section is tensioned. Without the centering provided by the slot 38, disengagement of at least one of the teeth 32 could follow. Stated otherwise, employing precision guide features in the anchoring head 30 maintains central elongate spring member 10 or section 112/122/130 etc. positioning to keep the oppositely-facing teeth 32 engaged with the spring member element. This enables the teeth 32 to support the tensile load applied or transmitted through beams 12 of the spring member together in a "parallel" (literally and figuratively) arrangement.

Figure 8:
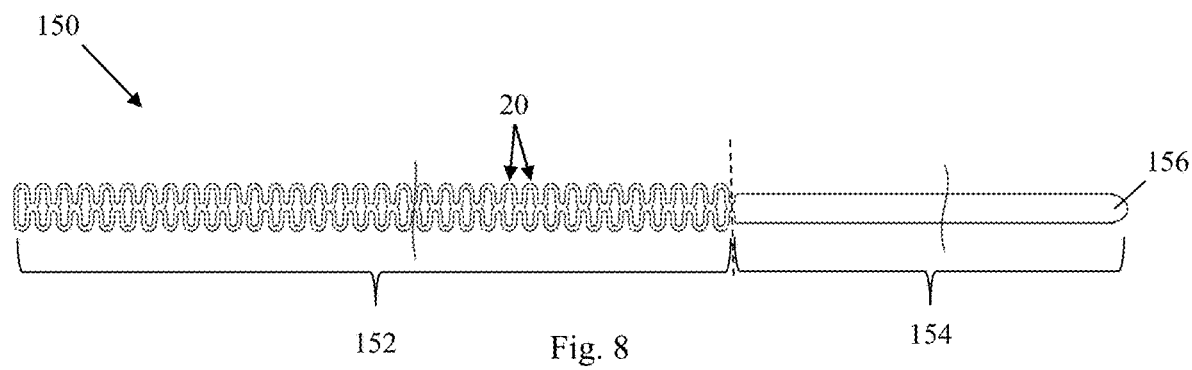
FIG. 8 is a top view of an example embodiment of an elongate spring member including an integral introducer.
Figure 9:
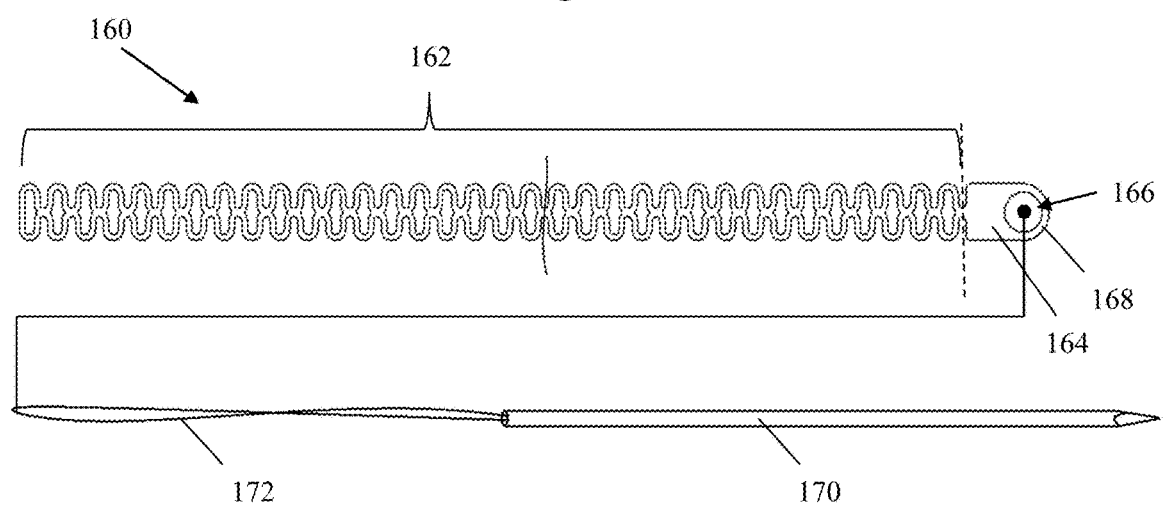
FIG. 9 is a top view of an example embodiment of an elongate spring member including a sacrificial tab with an eyelet for attachment of the needle or stylet introducer also pictured.
Figure 11A:
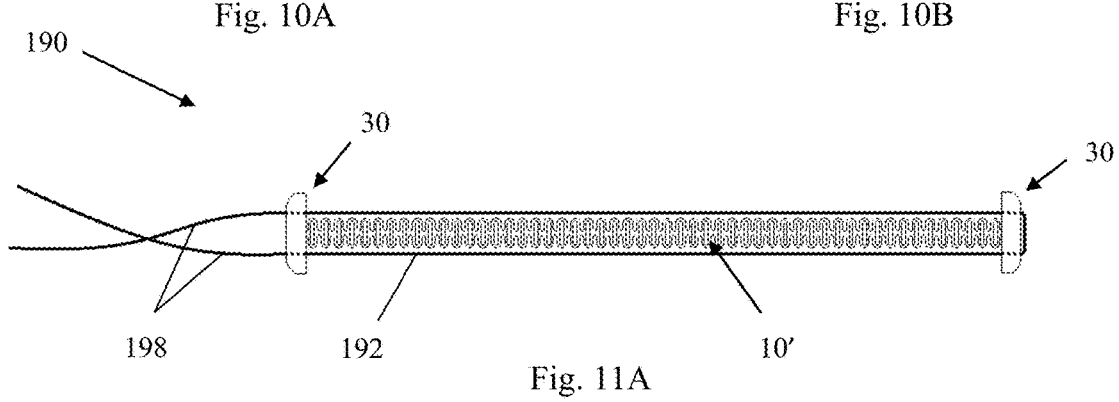
FIG. 11 is a face or top view of an example embodiment of a hybrid spring-member/suture-button device.

The spring member section or pattern 140 shown in FIG. 3 is configured to coordinate further with the guides 38 optionally provided in the anchoring head 30. Specifically, the pattern includes flattened sides 142. To produce these shapes, the external radii 144 of connections between adjacent beam pairs at their lateral extent may be minimized and/or the lateral connectors 16 between adjacent sets of beams lengthened. These (relatively extended) flat section(s) 142 provide further means of ensuring spring member guide slot retention. These features are optional, however, as even round-ended elongate spring member cells such as shown in FIGS. 8, 9, 11 and the above incorporated-by-reference disclosure are well-retained within the guide features.

Figure 4C:
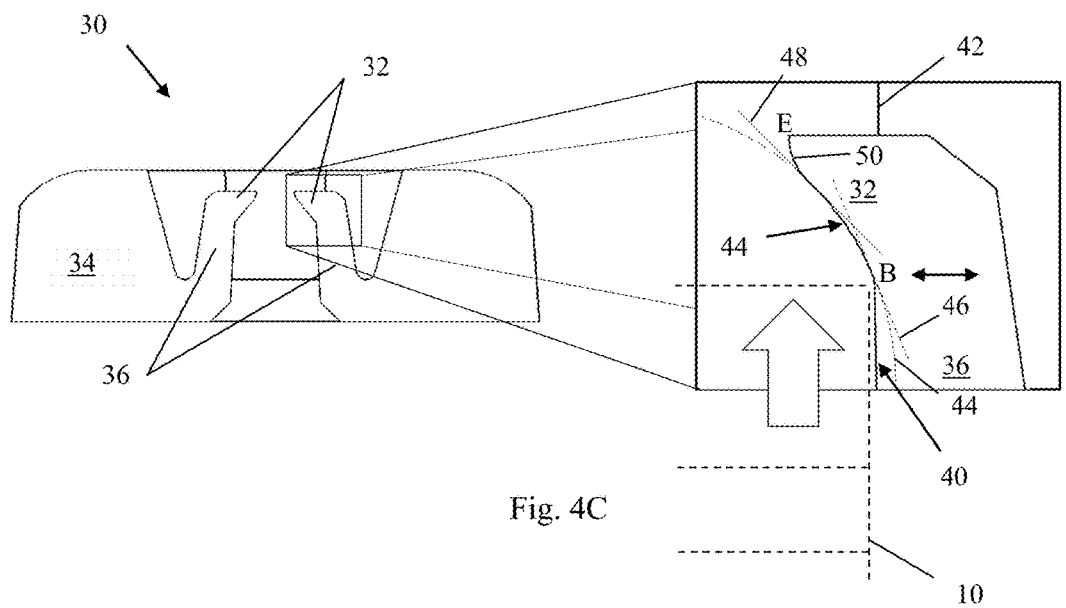

FIGS. 4A-4C further detail aspects of optional guide slots 38 as pictured. The detail view in FIG. 4C also illustrates an optional tooth 32 profile that eases elongate spring member loading into the anchor 30.

With an inner surface 40 of the support columns or beams 36 at or near vertical (e.g., within between about 2 and 5 degrees of vertical to provide draft angle for molding), each tooth 32 is configured to extend past the support column inner surface 40. Such a tooth configuration advantageously includes multiple faceted angles or a smooth radius or curve 44 to assist in its interaction with a spring member (a portion of spring member 10 is shown in phantom like) as it advances within the anchoring head 30.

As shown in the detail view of FIG. 4C, such a configuration can be appreciated in relation to tangent reference angles 46 and 48. In this respect, a steeper initial angle 46 (e.g., where an introduced elongate member 10, etc. has an initial contact angle between about 20 and about 30 degrees, see open arrow in connection with phantom line body 10 section) minimizes the force required to feed the elongate spring member into the anchoring head 30 and laterally displace the teeth 32 (with their support columns 36) for elongate spring member advancement (as indicated by the side-to-side arrow).

After the associated initial introduction angle (e.g., tangent with reference angle 44), the cross-section shape may transition or flatten to about 40 to about 60 degrees at or near a mid-point (e.g., a "mid-tooth" point plus as measured along its cross-sectional length from beginning (B) to end (E) within a range of about 5 to about 15% in either direction) of the tooth 32. Doing so increases the length of the tooth 32 (e.g., for a given height) fitting into cell apertures 22 (or otherwise) into the selected elongate spring member.

A final radiused section 50 may also (or alternatively, if used alone) be applied to the tooth 32 profile in order to protect its upper edge against abrasion and/or chipping (e.g., as compared to having the tooth 32 cross-section in the view of FIG. 4C end in a point). This can be particularly helpful as the tooth reciprocates (again, as indicated by the double-arrow) in and out of adjacent cells 20 of the elongate spring member as the anchor 30 is advanced over the same (or as the elongate spring member is pulled through the body, in a relative or absolute sense). As illustrated in FIG. 4C, these two contiguous or blended curves 44 and 50 may define the "feed" profile of each anchoring head tooth 32. With such a profile, no radius or taper need be applied to the elongate body 10, etc. to facilitate loading into the anchoring head 30. However, such processing remains an option.

Note that it is not desirable to start the tooth angle (is indicated by tangent line 46) at less than about 20 degrees. The reason for this is that doing so will simply increase the height of the tooth to be received within the openings 22 of the elongate member. Starting the angle at about 20 degrees or more results in the immediate application of an appreciable lateral component of force to deflect the support column 36 of each tooth 32. Yet, reduction from a 45 degree contact angle (e.g., as disclosed in the '022 patent application reference above) improves the mechanical advantage for introducing the elongate spring member as it ramps over the tooth surface. Doing so is particularly useful as this initial contact occurs with the least mechanical advantage (i.e., with the shortest lever-arm length) for deflecting each tooth support beam or column.

In any case, the teeth 32 and apertures or window cutouts 22 in the spring member are adapted to work together in a ratchet-type interface that allows advancement in one direction and holds a locked position in the other. To minimize height or profile of the anchoring head 30, it may be limited to having two teeth, directly opposite or facing one another, as shown. In other works, vertically stacking multiple teeth as common with zip ties is advantageously avoided—although not prohibited.

Figure 5A:
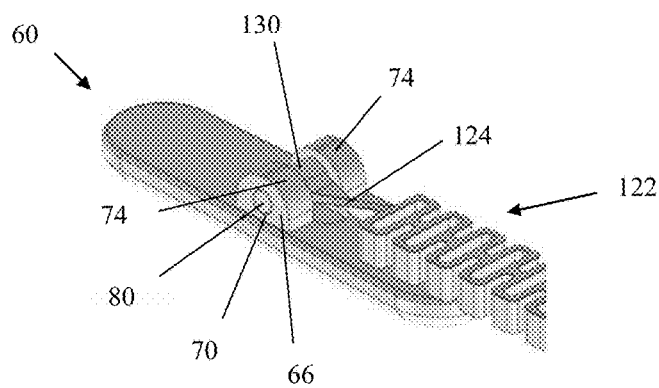
FIGS. 5A and 5B are perspective views of different anchoring foot embodiments.
Figure 5B:
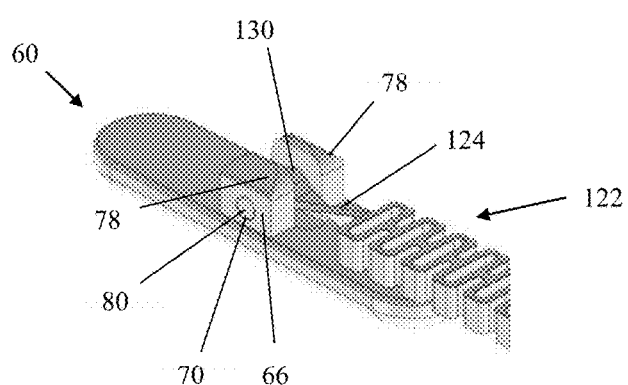
Figure 6:
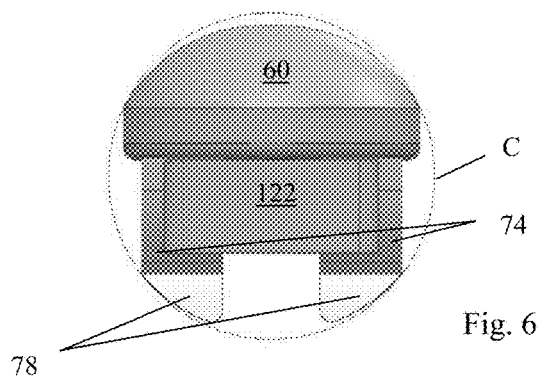
FIG. 6 is an end view of the same pieces shown in FIGS. 5A and 5B overlaid on one another.

FIGS. 5A and 5B are perspective views of different anchoring foot embodiments. They vary in terms of the configuration of their attachment boss sections. In the anchoring foot 60 shown in FIG. 5A, boss 66 is capped with a full radius or half-cylinder cap 74. In the anchoring foot 76 shown in FIG. 5B, the boss 66 features are more complex and include inward-angled bolsters or fins 78 that increase the available material to resist material failure by pin pull-through. So-configured, the fins 78 may be included within the same delivery profile or envelope (e.g., fit through the same diameter drill hole) as illustrated in connection with circle (C) in FIG. 6. With parts produced in poly-ethyl-ethyl-ketone (PEEK) the inclusion of fins 78 in the design has been shown to increase in strength from about 30 lbf to about 45 lb lbf (i.e., at least about 50%) when comparing the two designs.

With a complete medical device including either foot 60 or in a body-aligned or stowed configuration, the foot and elongate spring body can be inserted together through a minimum-diameter hole or channel spanning bone(s), joint space and/or a fracture. Then the system is secured or stabilized with the foot in a fully or partially transverse orientation, with the elongate body received in an anchoring head or otherwise clamped. Further optional method details are noted both above and below.

Digital or electronic features may also be included in the subject devices or systems. Electronics including digital memory, one or more computer processors (general or application-specific processors), displays (including external pads, monitors and smart phones) with or without associated computer processing features, and other ancillary hardware optionally form embodiments hereof. More specific electronic hardware is described further below.

Figure 7:
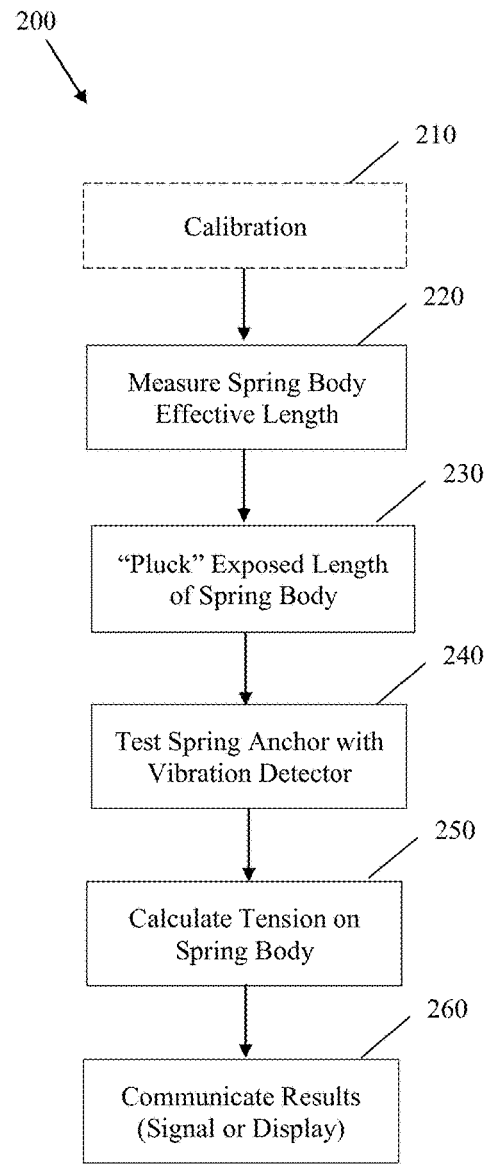
FIG. 7 is flowchart for an example embodiment of a digital tensioning system method.

As for the associated methodology, FIG. 7 presents a flowchart for a digital system tensioning method 200. The method operates on the principle of frequency harmonics for a system having known physical parameters. For an implanted device 100, 110, 120 or another like it, higher tension on the elongate spring member results in the spring member having a higher natural frequency or frequencies. With calibration performed in advance that relates the known configuration of the elongate spring member body (e.g., body 10, 116 or 126 the latter including extensions 114 and 124, respectively) to an implanted section of the spring body between its anchor points, tension on the member can be determined according to method 200. This calibration step is optionally included in the subject method at 210.

In any case, at 220, the effective length of the elongate spring member (i.e., its length between anchor points of contact) is measured. The measurement may be performed using dedicated calipers or in connection with a surgical clamp otherwise used for reducing the treatment sight. The length obtained may be measured between two head-type anchors 30 (e.g., as shown in FIG. 1A), or between one head-type anchor 30 and a foot anchor 60 (as shown in FIGS. 1B and 1C) or otherwise.

At 230 (with a device configuration, optionally, as shown in FIG. 1A before trimming its surplus body length 202 off flush with the anchor 30 to finish the device during implantation) the spring member body 10 is perturbed. To do so, length 202 may be plucked like a guitar string. At 240, an exposed anchor (typically, though not necessarily, a head-type anchor 30 on the same side as the plucked length 202 of the spring member body) is tested with a vibration detector. The spring frequency (at resonance) transmitted though the anchor is recorded.

To obtain this reading or measurement, any suitable sensor probe or detector may be employed. If a piezoelectric sensor probe is employed, the anchor will be contacted. For a non-contact method, a laser-based vibration detector may be employed.

At 250, the tension on the spring member body is estimated using the recorded frequency (which signal may be filtered for high frequency harmonics, alone), measured effective length and calibration information. Results are communicated or output at 260. The form the results output may vary in accordance with any desired user interface (UI).

For example, the estimated tension between anchors (or compression applied to the underlying anatomy by the anchors) may be output. Alternatively, a green light emitting diode (LED) may illuminate if proper tension is applied. If not, a user might tighten the anchor(s) and re-test starting at 220 or 230. Conversely, a red LED or other displayed alert might indicate over-tensioning. In which case, the surgeon might choose to cut off one anchor (e.g., using side cutters and cutting through its PEEK body) and apply a new anchoring head that is tensioned as desired.

Other optional embodiment features are shown in FIG. 8. Here, an elongate body 150 is shown that includes each of a spring member section or portion 152 with repeating cells 20 and integral introducer section 154. These portions are connected with a final medial connector or bridge 18. Other connection configurations are possible as well.

In this example, introducer 154 (optionally referred to as a needle, although it will typically be square or rectangular in profile if integrally cut with the spring pattern), is stiff and will pass straight though surgical incisions and drill-holes in bone and other soft tissue. Once passed, it can be trimmed off at the bridge 18 (as indicated by dashed line) and the remaining elongate spring body section 152 used just as spring member 10 in device 100.

Also, the introducer or needle section 154 may include an atraumatic tip 156 as pictured. Alternatively, it may be provided with a pointed (even sharpened) tip like the needle pictured in FIG. 9.

In FIG. 9, a system 160 a spring body section or portion 162 is connected to a tab 164 that optionally including an eyelet 166. A needle 168 for coordinated use may include suture ends swaged into a lumen of the needle to form a loop 170. In which case, one end of the suture forming the loop may pass through eyelet 166 formed in tab 164 before swaging.

Alternatively, the loop may be secured in the eyelet 168 with a Girth hitch or Prusik knot after formation. In yet another approach, the needle also includes an eyelet (not shown) and a loop (optionally formed with braided material using a long bury splice or simple knot to close the loop) connects the two eyelets.

Note that the suture material referenced above may include braided ultra-high-molecular-weight polyethylene (UHMWPE, UHMW) or other material. The same is true for the embodiment in FIG. 11.

In any case, after the attached needle (optionally referred to as a Beath needle) is used to pull the spring member into position during a medical procedure, tab 166 can be cut-off and discarded as with the needle in embodiment 150. The optional rounded-end 168 of the tab may assist in its passing through or past body tissue. However, the end may be more pointed or even flat.

Figure 10A:
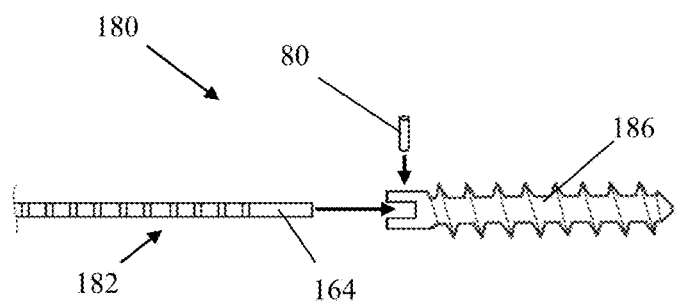
FIG. 10A is a side assembly view of a distal end of an example embodiment of a system in which an elongate spring member including a distal tab is fit into and secured with a screw head.
Figure 10B:
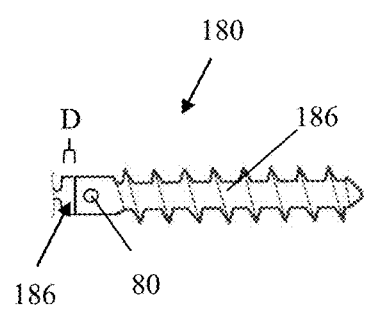
FIG. 10B is a face or top view of the distal end of the FIG. 10A construct.

The assembly 180 shown in FIGS. 10A and 10B advantageously use a flat-end tab version of the spring member shown in FIG. 9. This spring member 182 has its end tab 164 fit into a slot 184 and secured by a pin 80 within a screw head 186. In FIG. 10B, the manner in which tab 184 extends above the face or shoulder 188 of the screw provides drive surfaces (D) extending at least about 1 mm for interface with a complimentary driver tool or socket.

As referenced above, the system embodiment 190 in FIG. 11 includes suture material. One or two strands 192 of such material may be provided. As shown in this side view, they pass through a pair of anchors 30. To facilitate such use, the anchors may have through hole sets as picture in FIGS. 4A in 4B.

In FIG. 4A, a single set of holes 194 is provide in a positioned in places where ejector pin marks may be set. In which case, the holes can be drilled-out in a subsequent machining operation. However, they may be formed during injection molding. The same is true if two sets of holes locations 196A and 196B are provided as shown in FIG. 4B.

A single suture strand 192 is passed through each set of holes 194 in the pair of anchors 30 shown. Upon tying its loose ends 198, the anchors are captured within the resulting loop. If anchors are selected with two sets of holes 196A and 196B, two suture stands are used to produce two loops when tied down.

In any case, the elongate spring member section 10' (i.e., the full elongate spring member 10 or another, after trimmed to length) provides a constant tension upon preload application. The suture loops will limit maximum extension of the spring. Note also, that system 190 can be implemented with splice "ties" instead of knots as is well known in existing suture-button devices. As a hybrid approach, however, the elements in embodiment 190 work together to offer certain heretofore unknown advantages.

Medical Methods

With an injury (e.g., a fracture or sprain) reduced to an anatomic position, one or more of the subject device embodiments is installed via incision(s) and pre-drilled hole(s). After satisfactory tensioning (either preloading by pulling the spring member body through the anchor, pulling the spring member body and pushing the anchor forward, or simply by releasing the reduction with the anchors already snugged in place), any remaining end(s) of the elongates spring member is trimmed flush with associated anchor(s) using a commercially available cutter. Alternatively, a modified version of a cable tie tool or so-called "zip-tie gun" may be used to automatically or semi-automatically tighten and/or trim the system. However, preload application is accomplished, the subject devices remain active to provide continuous compression allowing for anatomical motion across a joint or provide a less stressful alternative to a stiff screw for a bone break. Finally, as referenced above, suitable methods of medical use also applicable to the present embodiments are described with respect to FIGS. 8-15 of the incorporated U.S. Publication No. 2016/0213368 and Int'l Publication No. WO 2016/122944.

Digital Hardware

The calculation or processes carried out in connection with the embodiments herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, USBC, Display Port, or any other form.

A processor may also be implemented as a combination of computing devices, e.g., a combination of a DSP and a microprocessor, multiple microprocessors, one or more microprocessors in conjunction with a DSP core, or any other such configuration. These devices may also be used to select values for devices as described herein. The camera may be a digital camera of any type including those using CMOS, CCD or other digital image capture technology.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, an optical disc, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be encoded as instructions and data in a non-transitory computer-readable medium, for example, a computer memory. When executed by a processor, the encoded instructions may cause an apparatus, for example a flow sensor, to perform a method as described herein. Computer-readable media includes both computer storage media and communication media including any medium that facilitates transfer of a computer program from one place to another. A non-transitory computer-readable medium may include any non-transitory medium suitable for access and decoding by a computer. By way of example, and not limitation, such non-transitory computer-readable media can include RAM, ROM, EEPROM, CD-ROM or other optical disk storage, magnetic disk storage or other magnetic storage devices, or any other medium that can be used to encode desired program code in the form of non-transitory instructions or data structures and that can be accessed by a computer. The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Operations as described herein can be carried out on or over a website. The website can be operated on a server computer or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Variations

The elongate spring members may be laser-cut in NiTi alloy that is superelastic at human body temperature (37° C.) or below and subsequently electropolished. Other material options for the spring member include β-titanium alloys, certain higher performance plastics including poly-ethelyethly-ketone (PEEK) or other materials with at least relatively high reversible strain properties. The anchors (heads or feet) may be molded in PEEK or machined in stainless steel or another material. Molded anchors optionally include markers or may be loaded with barium sulfate for radiopacity. Markers may take the form of discs or "pucks" pressed into pockets or may be in the form of a disc or rim attached to the marker. In the case of an anchor head, such a disc or rim is optionally round, in the case of an anchoring foot it may be oblong or racetrack shaped. Suitable marker materials include tantalum, stainless steel and even NiTi. Any cross pins used may be made of stainless steel, NiTi or another suitable metal alloy. The same is true of any screw heads, though they might alternatively be made of PEEK, especially if to be used in as a soft-tissue anchor. Many other material options exist and are not intended to limit the invention unless so-claimed.

Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein. Moreover, no limitations from the specification are intended to be read into any claims, unless those limitations are expressly included in the claims.

As used herein and in the appended claims, the singular forms "a", "an", and "the" include plural referents unless the context clearly dictates otherwise. In other words, use of the articles allow for "at least one" of the subject items in the description above as well as the claims below. The claims may exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

The subject matter described herein and in the accompanying figures is done so with sufficient detail and clarity to permit the inclusion of claims, at any time, in means-plus-function format pursuant to 35 U.S.C. Section 112, Part (f). However, a claim is to be interpreted as invoking this means-plus-function format only if the phrase "means for" is explicitly recited in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, acts, steps, or elements of the embodiments may be recited in or added to the claims, as well as negative limitations that define the inventive scope of the claims by features, functions, acts, steps, or elements that are not within that scope.

The invention claimed is:

1. A medical device comprising:
an elongate spring member including a plurality of lateral beams and a longitudinal extension from a distal extent of the beams, wherein the longitudinal extension is inset from an outer extent of the plurality of lateral beams and has a length to fit at least part of the ends of the anchoring foot inward of the outer extent when the anchoring foot is pivoted to align with the longitudinal extension; a distal end of the lateral extension including an aperture;
an anchoring foot including a first end, a second end and pivot holes therebetween; and
a pin received by the anchoring foot pivot holes and the aperture in the longitudinal extension.

2. The medical device of claim 1, wherein the plurality of lateral beams are orthogonal to an axis of the elongate spring member.

3. The medical device of claim 1, further comprising an anchoring head that interfaces with the plurality of lateral beams.

4. The medical device of claim 3, wherein the anchoring head and anchoring foot comprise PEEK polymer material.

5. The medical device of claim 3, wherein the anchoring head comprises two teeth directly across from one another and side slots configured to constrain elongate spring member movement therebetween.

6. The medical device of claim 5, wherein the teeth are carried by support columns that include a substantially vertical inner surface and work with the side slots to constrain movement of the elongate spring member.

7. The medical device of claim 1, wherein the anchoring foot is connected by a pin passing through a pair of bosses extending proximally from a proximal surface of the foot.

8. The medical device of claim 7, wherein each boss is capped with a full radius terminating at the proximal surface of the foot.

9. The medical device of claim 7, wherein each boss is capped by an inwardly-angled or curved fin.

10. The medical device of claim 1, wherein the spring member and the extension are produced in a single piece of material.

11. The medical device of claim 10, wherein the material comprises NiTi alloy that is superelastic at human body temperature.

12. The medical device of claim 11, wherein the spring member is electropolished.

13. A medical device comprising:
an elongate spring member having a longitudinal axis and including a plurality of lateral beams and a longitudinal extension from a distal extent of the beams, wherein the lateral beams form a plurality of cells to operate as spring elements in series, each cell including an aperture and connected to an axially adjacent cell by a medial connector, and wherein the longitudinal extension is inset from an outer extent of the plurality of lateral beams and has a distal end including an aperture;
an anchoring foot including a first end, a second end and pivot holes therebetween; and
a pin received by the anchoring foot pivot holes and the aperture in the longitudinal extension.

14. The medical device of claim 13, wherein the longitudinal extension is set twisted 90 degrees and a proximal surface of the anchoring foot aligns with a face of the elongate spring member when the anchoring foot is pivoted for deployment.

15. The medical device of claim 13, wherein the longitudinal extension has a length to fit at least part of the ends of the anchoring foot inward of the outer extent when the anchoring foot is pivoted to align with the longitudinal extension.

16. The medical device of claim 13, wherein the plurality of lateral beams are orthogonal to an axis of the elongate spring member.

17. The medical device of claim 13, further comprising an anchoring head that interfaces with the plurality of lateral beams.

18. The medical device of claim 17, wherein the anchoring head and anchoring foot comprise PEEK polymer material.

19. The medical device of claim 18, wherein the anchoring head comprises two teeth directly across from one another and paired with side slots configured to constrain elongate spring member movement therebetween.

20. The medical device of claim 19, wherein the teeth are carried by support columns that include a substantially vertical inner surface and engage with the paired side slots to constrain movement of the elongate spring member.

21. The medical device of claim 13, wherein the spring member and the extension are produced in a single piece of material.

22. The medical device of claim 21, wherein the material comprises NiTi alloy that is superelastic at human body temperature.

23. The medical device of claim 13, wherein the spring member is electropolished.

* * * * *